United States Patent
Isaza

(10) Patent No.: US 7,997,272 B2
(45) Date of Patent: Aug. 16, 2011

(54) VENTILATING APPARATUS AND METHOD ENABLING A PATIENT TO TALK WITH OR WITHOUT A TRACHOSTOMY TUBE CHECK VALVE

(75) Inventor: Fernando Isaza, Carlsbad, CA (US)

(73) Assignee: Ric Investments, LLC., Wilmington, DE (US)

( * ) Notice: Subject to any disclaimer, the term of this patent is extended or adjusted under 35 U.S.C. 154(b) by 1001 days.

(21) Appl. No.: 11/518,816

(22) Filed: Sep. 11, 2006

(65) Prior Publication Data
US 2008/0060646 A1    Mar. 13, 2008

(51) Int. Cl.
A62B 9/02    (2006.01)

(52) U.S. Cl. ......... 128/205.24; 128/204.18; 128/204.21; 128/207.14; 128/207.16

(58) Field of Classification Search ............. 128/204.21, 128/204.18, 205.24, 207.14–16, 207.15, 128/207.16
See application file for complete search history.

(56) References Cited

U.S. PATENT DOCUMENTS

| | | |
|---|---|---|
| 4,219,020 A | 8/1980 | Czajka |
| 4,280,492 A * | 7/1981 | Latham ................... 128/207.15 |
| 4,442,856 A | 4/1984 | Betz |
| 4,759,356 A | 7/1988 | Muir |
| 5,813,399 A | 9/1998 | Isaza et al. |
| 6,189,534 B1 * | 2/2001 | Zowtiak et al. .......... 128/207.16 |
| 6,230,708 B1 | 5/2001 | Radko |
| 6,401,713 B1 * | 6/2002 | Hill et al. ................. 128/204.21 |
| 6,543,449 B1 | 4/2003 | Woodring et al. |
| 6,626,175 B2 | 9/2003 | Jafari et al. |
| 6,668,824 B1 | 12/2003 | Isaza et al. |
| 6,823,866 B2 | 11/2004 | Jafari et al. |
| 7,156,090 B2 * | 1/2007 | Nomori .................... 128/200.26 |
| 7,617,824 B2 * | 11/2009 | Doyle ....................... 128/204.21 |
| RE41,345 E * | 5/2010 | Blom ........................ 128/207.14 |
| 2004/0123868 A1 | 7/2004 | Rutter |

FOREIGN PATENT DOCUMENTS

WO    WO 2004/084982    10/2004

* cited by examiner

Primary Examiner — Justine R Yu
Assistant Examiner — Kevin Chu

(57) ABSTRACT

A method of operating a ventilator assembly having inhalation and exhalation passages communicating with one another, and a respiration assembly that can perform repetitive respiratory cycles. The method includes (a) connecting the conduit with an open end of an endotracheal tube positioned within the trachea so that the open end leads into the airway below the vocal cords, (b) repetitively cycling the respiration assembly so that during the inhalation phase, gas in the inhalation passage flows through the endotracheal tube and into the airway, and during the exhalation phase, an exhalation valve is maintained relatively closed and the exhaled gases flow pass the vocal cords and out of the mouth thereby facilitating the patient's ability to speak, and (c) monitoring ring the pressure within at least one of the passages during both phases for determining the pressure within the patient for use in operating the ventilator assembly.

10 Claims, 10 Drawing Sheets

VENTILATING APPARATUS AND METHOD ENABLING A PATIENT TO TALK WITH OR WITHOUT A TRACHOSTOMY TUBE CHECK VALVE

BACKGROUND OF THE INVENTION

1. Field of the Invention

This application relates to ventilation of a patient, and, more particularly, to a method and apparatus for invasive ventilation of a patient utilizing an endotracheal tube assembly and a ventilator assembly.

2. Description of Related Art

An example of a known endotracheal tube assembly is disclosed in U.S. Pat. No. 4,759,356 ("the '356 patent"), the entire disclosure of which is hereby incorporated by reference into the present specification. An example of a known ventilator assembly is disclosed in U.S. Pat. No. 6,543,449 ("the '449 patent"), the entire disclosure of which is hereby incorporated by reference into the present specification.

The endotracheal tube assembly disclosed in the '356 patent includes an endotracheal tube configured to be installed into a patient's trachea so that an inner open end communicates with the patient's airway and lungs and an outer open end is suitably anchored exteriorly of the patient's neck. The '356 patent discloses the provision of a check valve on the open end of the tube, often referred to in the art as a "talking valve." The check valve disclosed in the '356 patent is in widespread use and the '356 patent specification indicates many advantages of the check valve when in use in addition to the basic talking advantage function.

The ventilator assembly disclosed in the '449 patent has the capability of invasive use, as with an endotracheal tube assembly, or non-invasive use, as with a mask. The present invention focuses on the invasive mode of ventilator operation.

As stated in the '356 patent, there are many advantages in addition to the talking capability which result from the use of a check valve. However, there are disadvantages as well. For example, the check valve should be removed in order to give the patient aerosol treatments or to perform suctioning.

SUMMARY OF THE INVENTION

The present invention relates to a method by which the advantages of a check valve in a endotracheal tube can be obtained without the disadvantages thereof. The method of the invention relates to a method of operating a ventilator assembly having conduit providing inhalation and exhalation passages communicating with one another, and a respiration assembly capable of performing repetitive respiratory cycles each including (1) an inhalation phase during which an inhalation valve in the inhalation passage is relatively open for the passage of gas therethrough into the inhalation passage and to patient and an exhalation valve between the exhalation passage and an exhalation outlet in the ventilator assembly is relatively closed and (2) an exhalation phase during which the inhalation valve is relatively closed.

In an exemplary embodiment, the method comprises the steps of connecting the conduit with an exterior open end of an endotracheal tube positioned within a patient's trachea so that an interior open end leads into the patient's airway and lungs below the patient's vocal cords. The respiration assembly is repetitively cycles so that during the inhalation phase, the gas in the inhalation passage flows through the endotracheal tube and into the patient's airway and lungs, and during the exhalation phase, the exhalation valve is maintained relatively closed and the patient is allowed to exhale the gases in the patient's airway and lungs, passed the patient's vocal cords and out of the patient's mouth, thereby facilitating the patient's ability to speak. The pressure within at least one of the passages is monitored during both phases for purposes of determining the pressure within the patient's airway and lungs for use in operating the ventilator assembly.

In one embodiment of the invention, the endotracheal tube is devoid of a check valve so that the gas exhaled by the patient during each exhalation phase is communicated with the passages while both inhalation and exhalation valves are closed.

The invention also includes a patient ventilating apparatus for carrying out the method as described above. The apparatus comprises the combination of the following components. An endotracheal tube constructed and arranged to be installed through a patient's trachea below the patient's vocal cords so that an exterior open end thereof is exterior of the patient and an interior open end thereof communicates with the patient's airway and lungs. A ventilator assembly is provided which includes conduit connected with the exterior open end of the endotracheal tube providing inhalation and exhalation passages communicating with one another. Inhalation and exhalation valves are mounted in the inhalation and exhalation passages, respectively.

The ventilator assembly is constructed and arranged to provide repetitive respiratory cycles, each including an inhalation phase during which the inhalation valve is relatively open and the exhalation valve is relatively closed and a flow of gas is allowed to pass through the inhalation passage and the endotracheal tube into the patient's airway and lungs. A controller is also provided for operating the inhalation valve and the exhalation valve, and the exhalation valve operates in a selected one of the following two exhalation phase modes: (1) a first mode wherein the exhalation valve is relatively open during the exhalation phase allowing the gas in the patient's airway and lungs after the preceding inhalation phase to pass through the open exhalation valve and an outlet of the ventilator assembly; and (2) a second mode wherein the exhalation valve is maintained relatively closed and the patient causes the gas in the patient's airway and lungs after the preceding inhalation phase to flow passed the patient's vocal cords and out of the patient's mouth, thus facilitating patient's ability to talk.

The ventilator assembly also includes a pressure monitoring structure operatively associated with the passages for purposes of determining the existing pressure conditions in the patient's airway and lungs for use by the controller in operating the ventilator assembly. In one embodiment, the endotracheal tube is devoid of a check valve so that the communication between the passages and the patient's airway and lungs while the exhalation valve is in the non-talking mode thereof is through the endotracheal tube open end in both directions.

As indicated above, utilizing an endotracheal tube devoid of a check valve is an aspect of the present invention which secures the talking function without the known disadvantages of check valves. Nevertheless, another aspect of the present invention resides in providing a ventilating apparatus which overcomes many of the known disadvantages of the use of a check valve even though a check valve is present in the endotracheal tube.

In another embodiment of the invention, the ventilating apparatus includes the following components. An endotracheal tube constructed and arranged to be installed into a patient's trachea below the patient's vocal cords so that an exterior open end thereof is exterior of the patient and an interior open end thereof communicates with the patient's airway and lungs. A ventilator assembly including conduit connected with the exterior open end of the tube and providing inhalation and exhalation passages communicating with one another, inhalation and exhalation valve in the inhalation and exhalation passages, respectively, and a respiration assembly constructed and arranged to provide repetitive respiratory cycles, each including (1) an inhalation phase during which an inhalation valve in the inhalation passage is relatively open and an exhalation valve in the exhalation passage is relatively closed and a flow of gas is allowed to pass through the inhalation passage and the tube into the patient's airway and lungs and (2) an exhalation phase during which the inhalation valve is relatively closed and the exhalation valve is maintained relatively closed.

The endotracheal tube has a check valve in the exterior open end thereof enabling the patient at the end of each inhalation phase to cause the gas in the patient's airway and lungs to pass through the patient's vocal cords and out of the patient's mouth, thus facilitating the patient's ability to speak, the check valve is operable to trap the pressure conditions within the passages at the end of the inhalation phase when both valves are relatively closed so as to allow the trapped pressure conditions in the passages at the end of each inhalation phase to equalize with the pressure conditions within the patient's airway and lungs during the exhalation phase. The ventilator assembly includes a pressure monitoring structure/ assembly for monitoring the pressure conditions in the passages during both phases for purposes of determining the existing pressure conditions in the patient's airway and lungs for use in operating the ventilator assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1A:
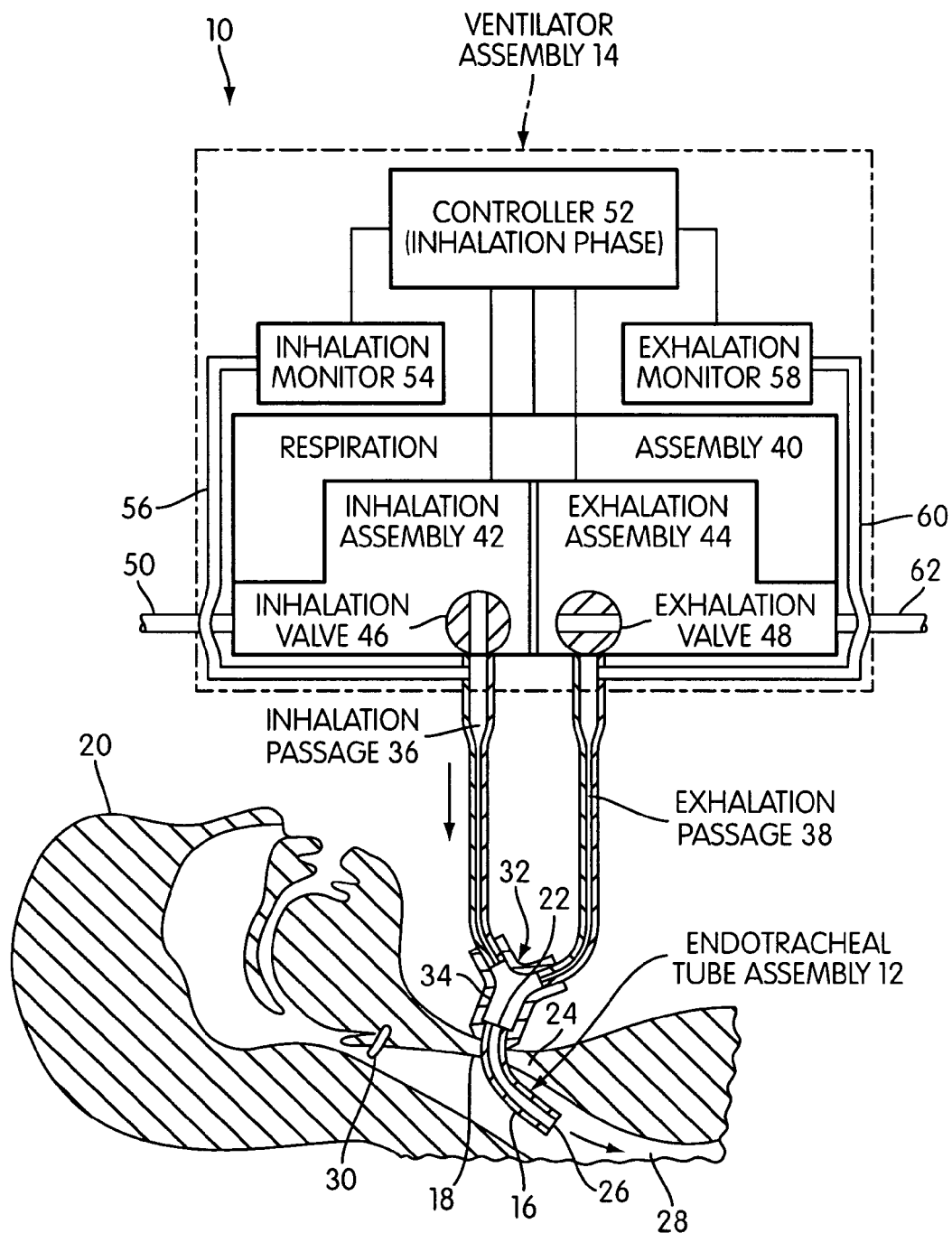
FIG. 1A is a partially schematic view of an embodiment of a ventilating apparatus according to one aspect of the invention, the apparatus being shown operatively connected with a patient with arrows indicating the direction of gas flow when the valves and controller are in an inhalation phase.

Referring now more particularly to FIGS. 1A, 1B, 2A, 2B, and 3 (or "FIGS. 1-3" for short) of the drawings, there is shown a ventilating apparatus, generally indicated at 10, embodying the principles of the present invention. Ventilating apparatus 10 includes, in general, an endotracheal tube assembly, generally indicated at 12, and a ventilator assembly, generally indicated at 14.

Endotracheal tube assembly 12 includes an endotracheal tube 16, constructed, for example, in accordance with the principles disclosed in the incorporated '356 patent. Endotracheal tube 16 is constructed and arranged to be mounted in a trachea 18 of a patient 20, as shown in FIGS. 1-3, so that an exterior open end 22 is suitably fixed in position exteriorly of the patient's neck 24 and an interior open end 26 communicates with the patient's airway and lungs 28 at a position below the patient's vocal cords 30.

Figure 2A:
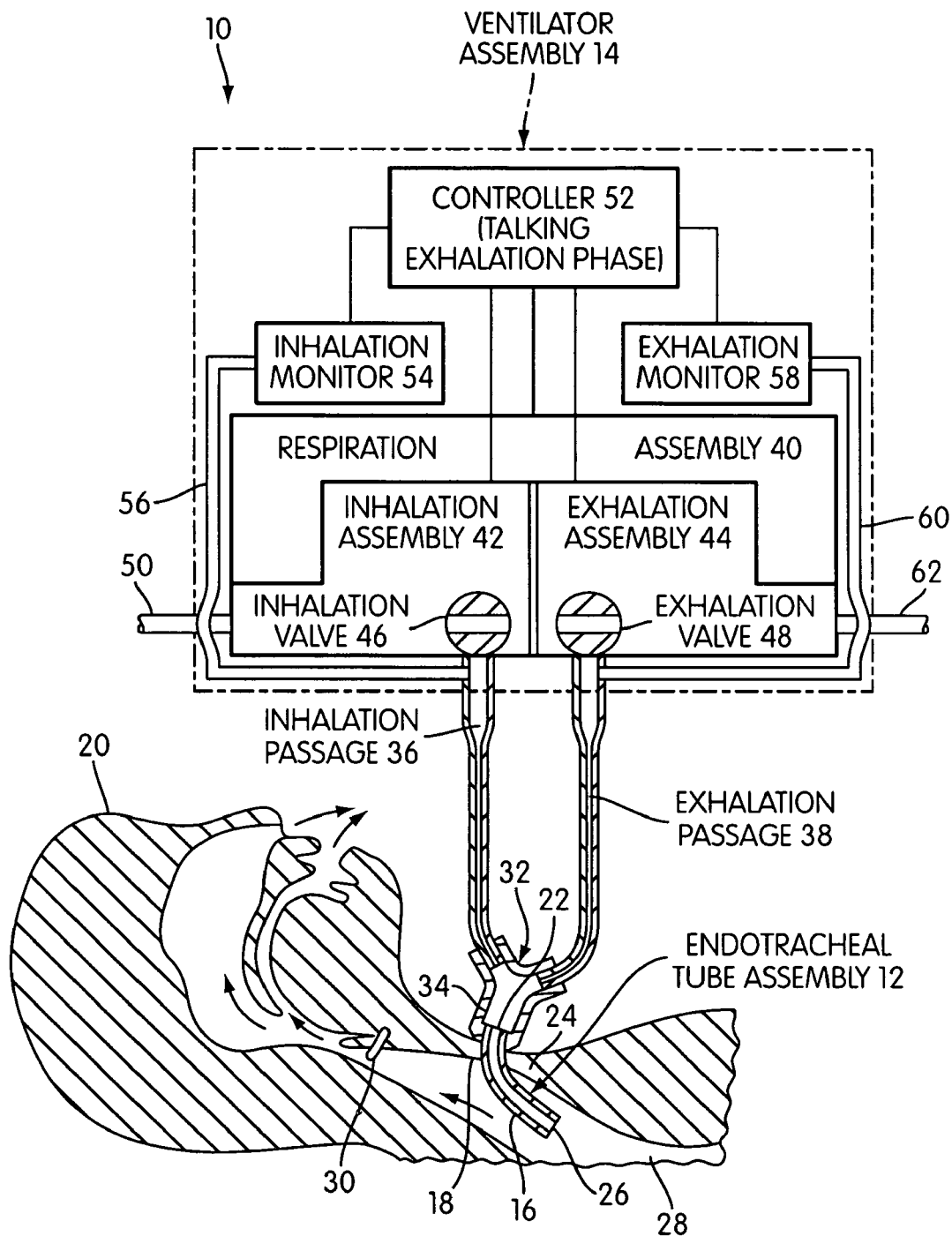
FIG. 2A is a partially schematic view of the embodiment of FIG. 1A, but showing arrows indicating the direction of flow when the valves and controller are in a talking mode exhalation phase.
Figure 2B:
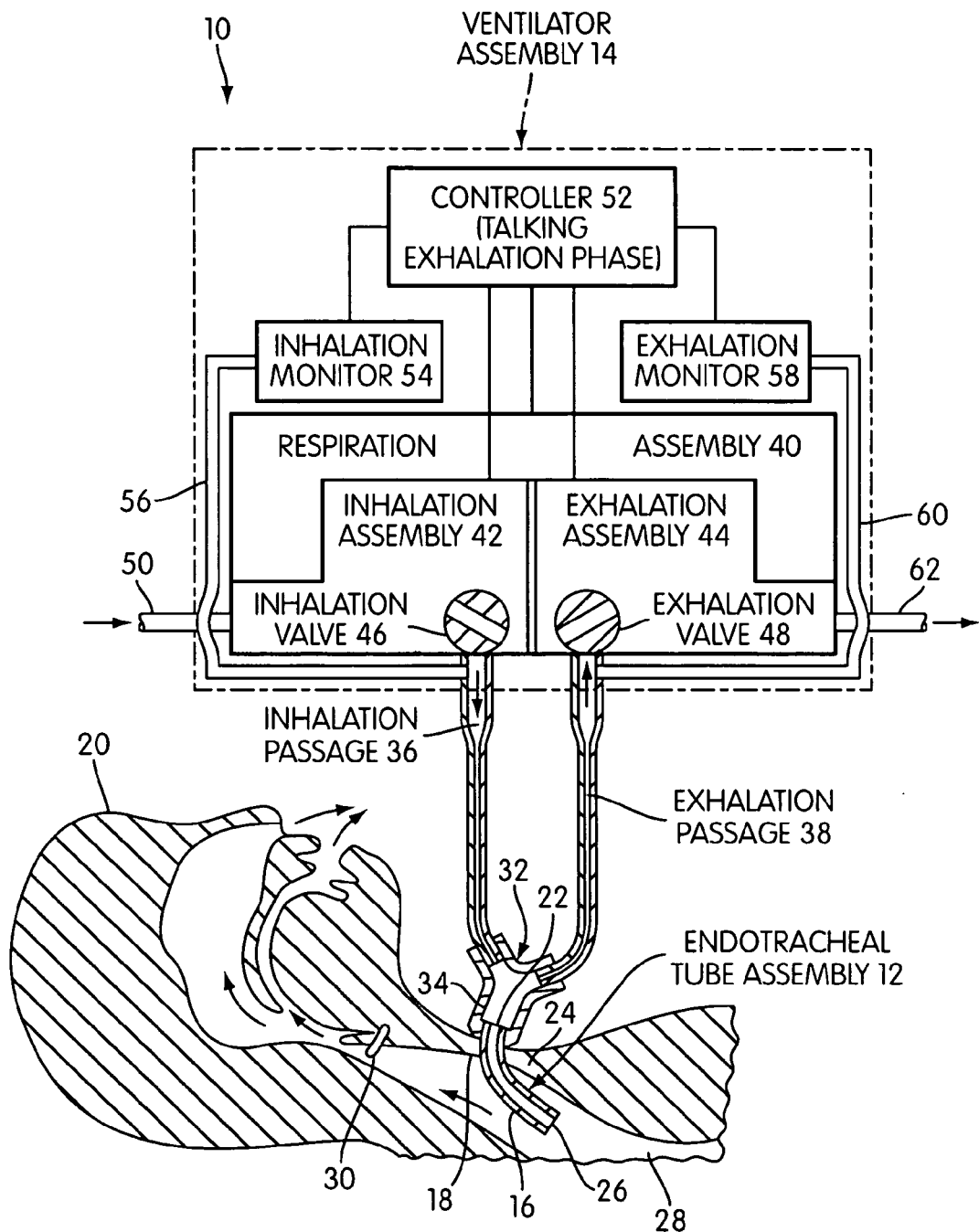
FIG. 2B is a view similar to 2A, but showing a partially closed exhalation valve and a partially closed inhalation valve.
Figure 3:
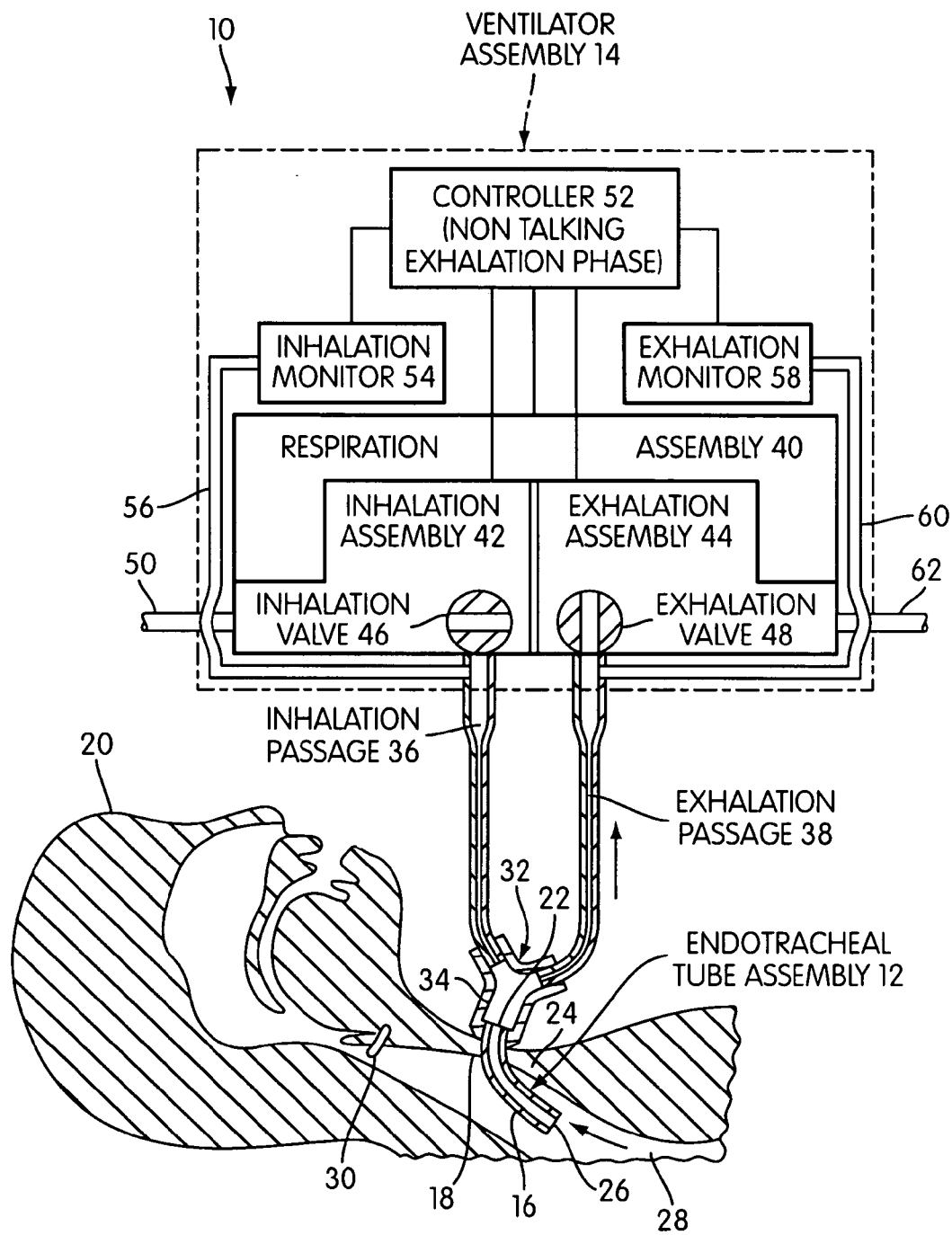
FIG. 3 is a partially schematic view of the embodiment of FIG. 1A, but showing arrows indicating the direction of flow when the valves and controller are in a non-talking mode exhalation phase.

In FIGS. 1-3, endotracheal tube 16 is shown as being devoid of a check valve, often referred to as the talking valve, such as the one disclosed in the '356 patent. Ventilator assembly 14 includes a conduit assembly, generally indicated at 32, which includes a Y fitting 34 and tubing portions forming an inhalation passage 36 and an exhalation passage 38, as will be described below. The stem of Y fitting 34 is connected over exterior open end 22 of endotracheal tube 16 so that endotracheal tube is devoid of a check valve and communicates with conduit assembly 32 for gaseous flow therethrough in either direction.

One branch of the Y fitting is connected with the tubing or conduit section defining inhalation passage 36 and the other branch of the Y fitting is connected with the tubing or conduit section defining exhalation passage 38. As can be seen from FIGS. 1-3, Y fitting 34 serves to communicate inhalation passage 36 and exhalation passage 38 with one another.

Conduit assembly 32 thus far described is disposed exteriorly of ventilator assembly 14, as indicated by broken lines in FIGS. 1-3. Ventilator assembly 14 houses a respiration assembly 40 therein which includes an inhalation assembly 42 and an exhalation assembly 44. In FIGS. 1-3, inhalation assembly 42 and exhalation assembly 44 of respiration assembly 40 are shown schematically in a block diagram. The gas flow components included in inhalation and exhalation assemblies 42 and 44 of respiration assembly 40 can be of conventional construction. A specific disclosure of one embodiment of the components used in accordance with the principles of the present invention is disclosed in the '449 patent.

As illustrated, inhalation assembly 42 includes a controllable inhalation valve 46 that communicates with inhalation passage 36, and exhalation assembly 44 includes a controllable exhalation valve 48 that communicates with exhalation passage 38.

Valves 46 and 48 are preferably controlled electronically by a controller 52 and are capable of being controlled to move between fully closed and fully open and any position of partial opening therebetween. Valves 46 and 48 can be of any suitable type for ventilator applications, such as proportional solenoid type valves, or stepper motor driven type, just for example.

Respiration assembly 40 is constructed and arranged to be controlled to provide repetitive respiratory cycles. Each respiration cycle includes an inhalation phase during which inhalation valve 46 is open and exhalation valve 48 is closed. During each inhalation phase, inhalation assembly 42 is controlled by controller 52 to cause a flow of gas to pass through the open inhalation valve 46, inhalation passage 36, endotracheal tube 16 into the patient's airway and lungs 28. In one embodiment, the flow of gas includes air and oxygen mixed by inhalation assembly 42 from a supply of air drawn through an inlet 50 of inhalation assembly 42 and a supply of oxygen contained within inhalation assembly 42. However, any known source of gas can be used and communicated through inhalation passage 36 via inhalation valve 46.

Each respiration cycle also includes an exhalation phase during which inhalation valve 46 is closed or partially closed (i.e., "relatively" closed as discussed later).

As best shown in FIGS. 2A and 2B, in accordance with an embodiment of the invention, exhalation valve 48 is controlled by controller 52 to remain in its relatively closed position, or to dynamically control the pressure in conduit assembly 32 in accordance with a desired pressure profile, during the exhalation phase, with the pressure profile being based upon the objective of enhancing the patient's ability to speak. This control of exhalation valve 48 enables the exhalation phase to be one in which the ability of the patient to talk is facilitated, even though there is no check valve embodied in endotracheal assembly 12 or conduit assembly 32. Thus, during the exhalation phase, when the patient is able to exhale the breathable gas introduced into the patient's airway and lungs in the preceding inhalation phase, the relatively closed inhalation and exhalation valves 46 and 48 prevent flow therebeyond, or are controlled to achieve a pressure profile in conduit assembly 32, so that the exhaled gas must flow passed the patient's vocal cords 30 on its way out of the patient's mouth, thus facilitating the patient's ability to talk, as shown by the arrows in FIGS. 2A and 2B.

Figure 1B:
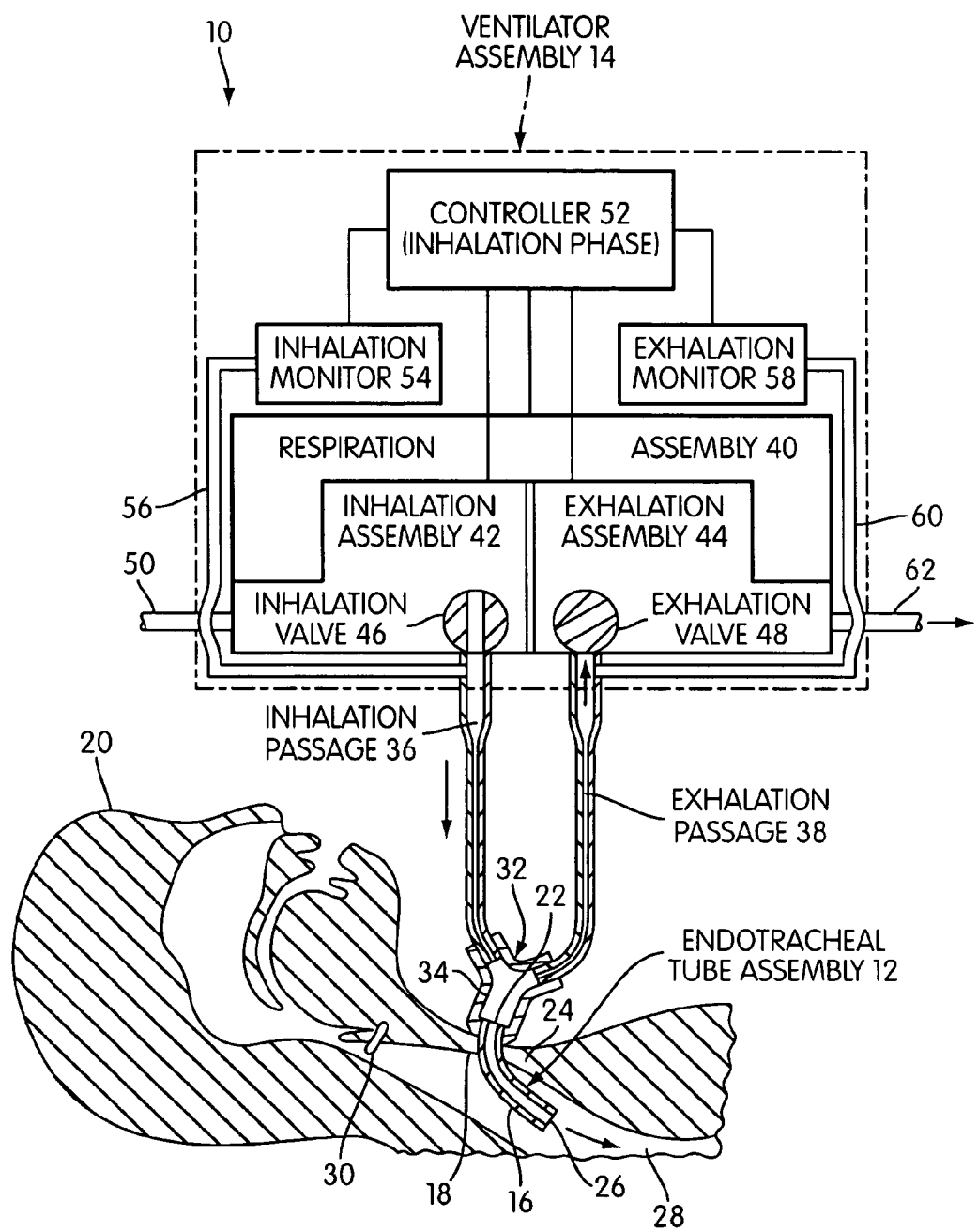
FIG. 1B is a view similar to 1A, but showing a partially closed exhalation valve.

It should be appreciated that in instances in which the inhalation valve or exhalation valve is disclosed herein as being "closed" or "open," this is not meant to necessarily refer to an absolute or fully open or fully closed valve (although it may), but rather a relational open or closed valve. In other words, for example, when the exhalation valve is "closed", this does not mean that it is completely closed to prevent any gas passage therethrough, as shown in FIGS. 1A and 2A. Rather, the exhalation valve may be partially closed, but closed sufficiently to achieve its desired functionality (as shown in FIGS. 1B and 2B). Thus, for example, a "relatively closed" or "relatively open" exhalation valve means a relatively closed position and a comparatively, relatively open position, respectively, as it relates to that particular valve. Similarly, a "closed" or "open" inhalation valve refers to two relative positions of the inhalation valve, wherein one position is relatively closed or relatively open with respect to the other. Thus, the term "relatively closed" as used herein is intended to convey this broad understanding and meaning.

In the inhalation phase, for example, the exhalation valve need not be fully closed, but may be closed only enough to enable a desired pressure to build within conduit assembly 32 and the patient's lungs. Similarly, in the inhalation phase, the inhalation valve need not be fully open, but may be open only enough to draw sufficient gas into conduit assembly 32 and patient's lungs to enable the patient to breath (not shown in the FIGS.). Similarly, in the exhalation phase, the inhalation valve need not be fully closed, but may be partially closed (see FIG. 2B), and the exhalation valve need only be closed sufficiently to maintain a desired profile of pressure in conduit assembly 32 (see FIG. 2B).

In one embodiment, the degree of opening and closing of the exhalation valve and/or inhalation valve is dynamically controlled by controller 52. Specifically, exhalation monitor 58 and/or inhalation monitor 54 can be used to monitor pressure throughout, or periodically during, the inhalation and/or exhalation phase and send a signal to controller 52 to continuously or intermittently send signals to open and/or close exhalation valve 48 and/or inhalation valve to a desired degree, based on a desired pressure to be provided within conduit assembly 32 or desired bleed rate through associated valve 46 and/or 48 at any point in the breathing cycle, or based upon the talking or non-talking mode of operation. In one embodiment, an encoder or any type of transducer can be used to measure the degree of valve opening and send feedback signals back to controller 52.

In one embodiment, during the inhalation phase, exhalation valve 48 is relatively closed (i.e., closed sufficiently to allow a desired amount of breathable gas to be provided to the patient), but may be only partially closed so as to be able to bleed excess gas (e.g. between about 3 to 7 liters per minute) through outlet port 62 (see FIG. 1B). In addition, inhalation valve 46 may be fully open or partially open, but in any event, relatively open in comparison when it is in the closed or relatively closed positions.

In one embodiment, during the exhalation phase, the exhalation valve and the inhalation valves are relatively closed, but one or both valves can be partially closed (see FIG. 2B) to control the level or pressure in conduit assembly 32. For example, in one embodiment it may be desirable to maintain the pressure in conduit assembly 32 above a specified threshold, such as, in one embodiment, 5 centimeters of water. Such control is often referred to as positive and expiratory pressure (PEEP), which can be used in the present invention, and as disclosed in U.S. Pat. No. 6,823,866, hereby incorporated by reference in its entirety. This method can be used to keep pressure within conduit assembly 32 above a certain level to keep the patient's airway open and/or enhance the patient's ability to speak.

It will be noted that while there is no flow through the communicating inhalation and exhalation passages 36 and 38 when valves 46 and 48 are closed in the exhalation phase, the communication provided by endotracheal tube 16 is such that passages 36 and 38 reflect the airway pressure during the exhalation phase just as they do during the inhalation phase.

In one embodiment controller 52 may be a programmable microprocessor and, as noted above, serves to control the operation of respiration assembly 40 in providing the repetitive respiration cycles, including control of inhalation assembly 42 and inhalation valve 46 thereof and exhalation assembly 44 and exhalation valve 48 thereof.

Controller 52, in its control of the overall operation of ventilator assembly 14, uses data relating to the measured pressure within the patient's airway as reflected in inhalation and exhalation passages 36 and 38. While the measured data could be obtained from a single monitor, in the illustrated embodiment two monitors are provided, including a inhalation monitor 54 communicated with inhalation passage 36 by suitable tubing 56, and a separate exhalation monitor 58 communicated with exhalation passage 38 by suitable tubing 60. In one embodiment, monitors 54 and 58 use pressure transducers capable of sensing the pressure conditions of the communicating passage and converting the sensed pressure condition into a discrete signal capable of being received and used by controller 52. Controller 52 opens and closes valves 46 and 48 based upon monitor 54 and/or monitor 58, the output of which can be used to detect the phase of respiration that the patient is in. That is, the monitors track the pressure within the patient's lungs throughout the breathing cycle to control opening and closing of valves 46 and 48.

In one embodiment, the controller uses two distinct algorithms, one for controlling exhalation valve 48 and the other for controlling inhalation valve 46. In another embodiment, the controller comprises two separate control units or control modules, one for controlling each valve and connected with at least one of monitors 54 and 58.

From the above, it will be understood that controller 52 is programmed so that during each exhalation phase, a talking mode is entered in which the exhalation valve remains closed or partially closed, as previously described.

In addition, the controller is programmed so that during the exhalation phase, a non-talking mode may be entered into, in which the exhalation valve is opened. In this non-talking mode (or "first" mode), the gas in the patient's airway and lungs at the end of the inhalation phase is allowed to flow through endotracheal tube 16, open exhalation valve 48 and out of an outlet 62 provided by exhalation assembly 44, as shown by the arrows in FIG. 3. The non-talking exhalation phase is entered into when monitor 54 and/or 58 sends a signal to controller 52 indicating a prescribed condition. For example, if monitor 54 and/or 58 detects that pressure in conduit assembly 32 is not being reduced at an expected rate, it may be indicative of a blockage (e.g., gas is being forced back into conduit assembly 32 rather than past the vocal chords) or airway occlusion. In this case, exhalation valve 48 will be open to allow gas to escape from the patient's lungs.

From the above, it can be seen that ventilating apparatus 10, as described above, facilitates the ability of the patient to talk when in the talking mode (or "second" mode) as shown in FIG. 2, and also provides a non-talking ventilation mode (see FIG. 3) merely by operation of controller 52 of FIG. 3. It should be appreciated that some talking may be possible in the first (or "non-talking") mode, although it may not be as conducive.

Referring now more particularly to FIGS. 4A, 4B, 5A and 5B (or "FIGS. 4 and 5" for short), there is shown therein an alternate embodiment. In this embodiment, endotracheal tube assembly 12 includes a conventional check valve 64 in conduit assembly 32. This embodiment demonstrates that the feature of enabling controller 52 to select a mode in which exhalation valve 48 is maintained in a relatively closed position during the exhalation phase can secure advantages even when a conventional check valve 64 is employed.

In the embodiment of FIGS. 4 and 5, controller 52 operates in a talking mode similar to the talking mode described above. The difference is that gas flow communication from the patient to ventilator assembly 14 during the exhalation phase is cut off at check valve 64 rather than at the relatively closed exhalation valve 48. If controller 52 actually functioned to open exhaust valve 48 during the exhalation phase as in the FIG. 3 non-talking mode, the pressure in exhalation passage 38 would simply be at atmospheric pressure during the exhalation phase so that exhalation monitor 58 would not be monitoring the patients airway pressure during the exhalation phase.

Figure 4A:
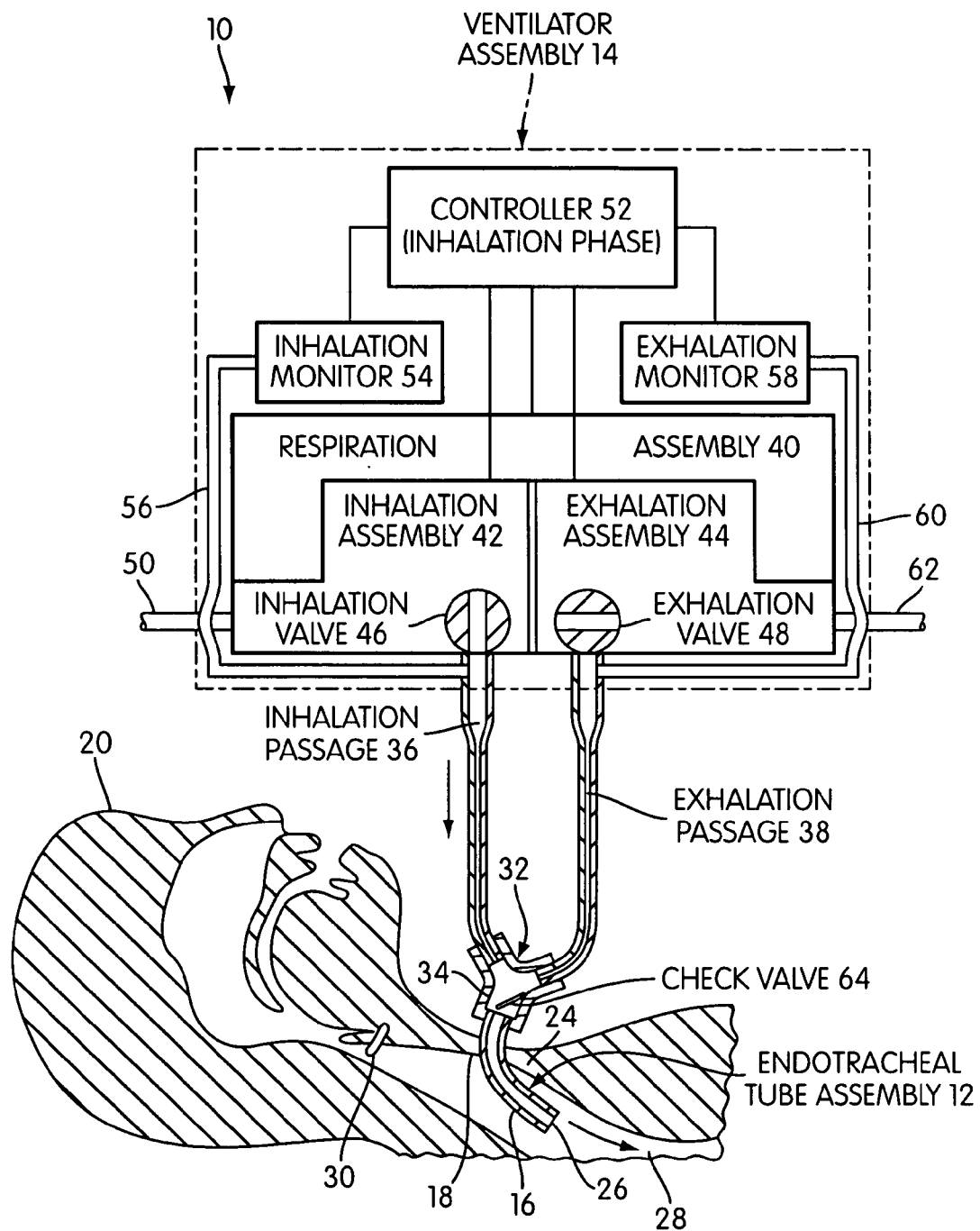
FIG. 4A illustrates another embodiment of the present invention wherein the endotracheal tube, rather than being devoid of a check valve as in FIG. 1A, has a check valve in the open end thereof.
Figure 4B:
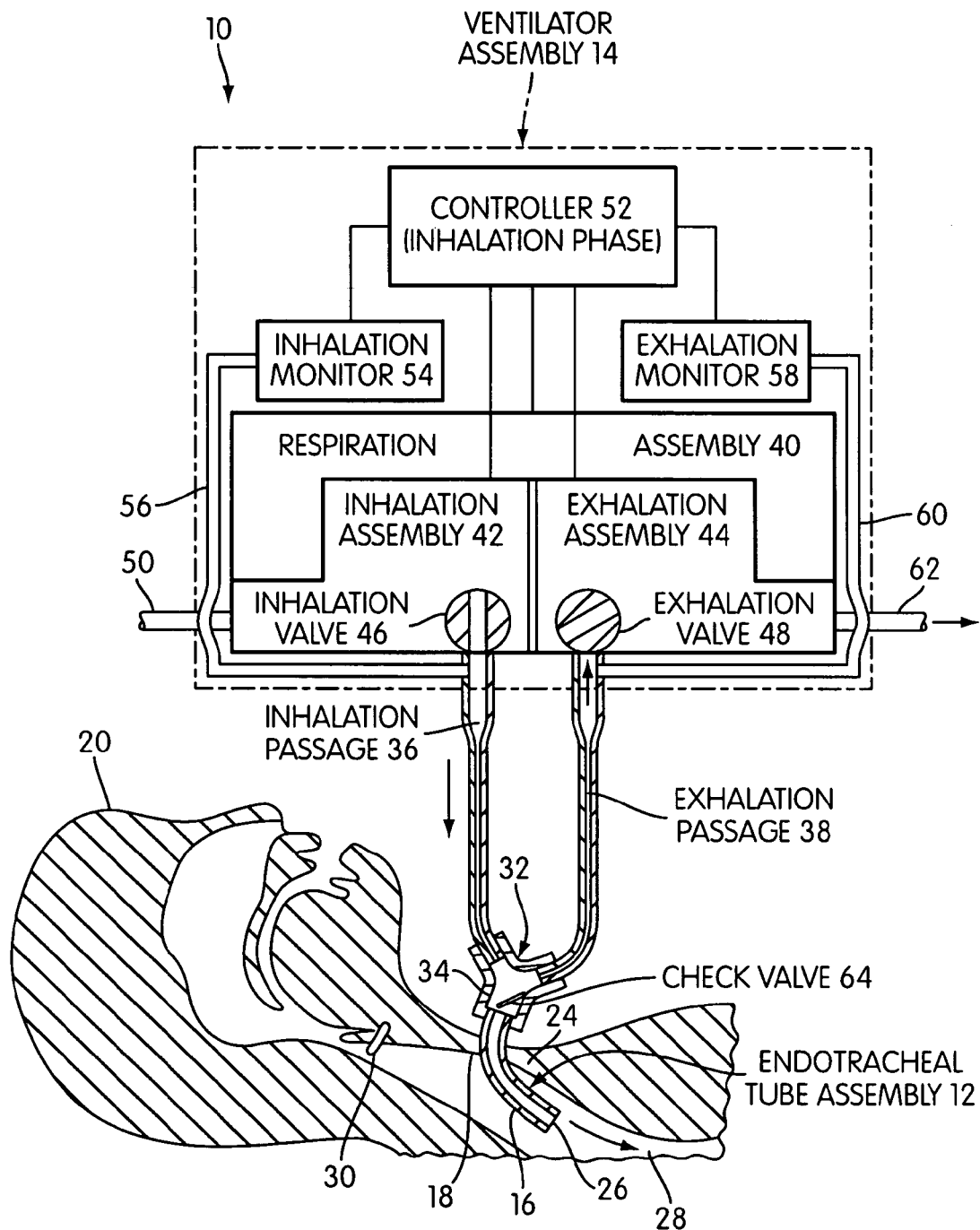
FIG. 4B is a view similar to 4A, but showing a partially closed exhalation valve.
Figure 5A:
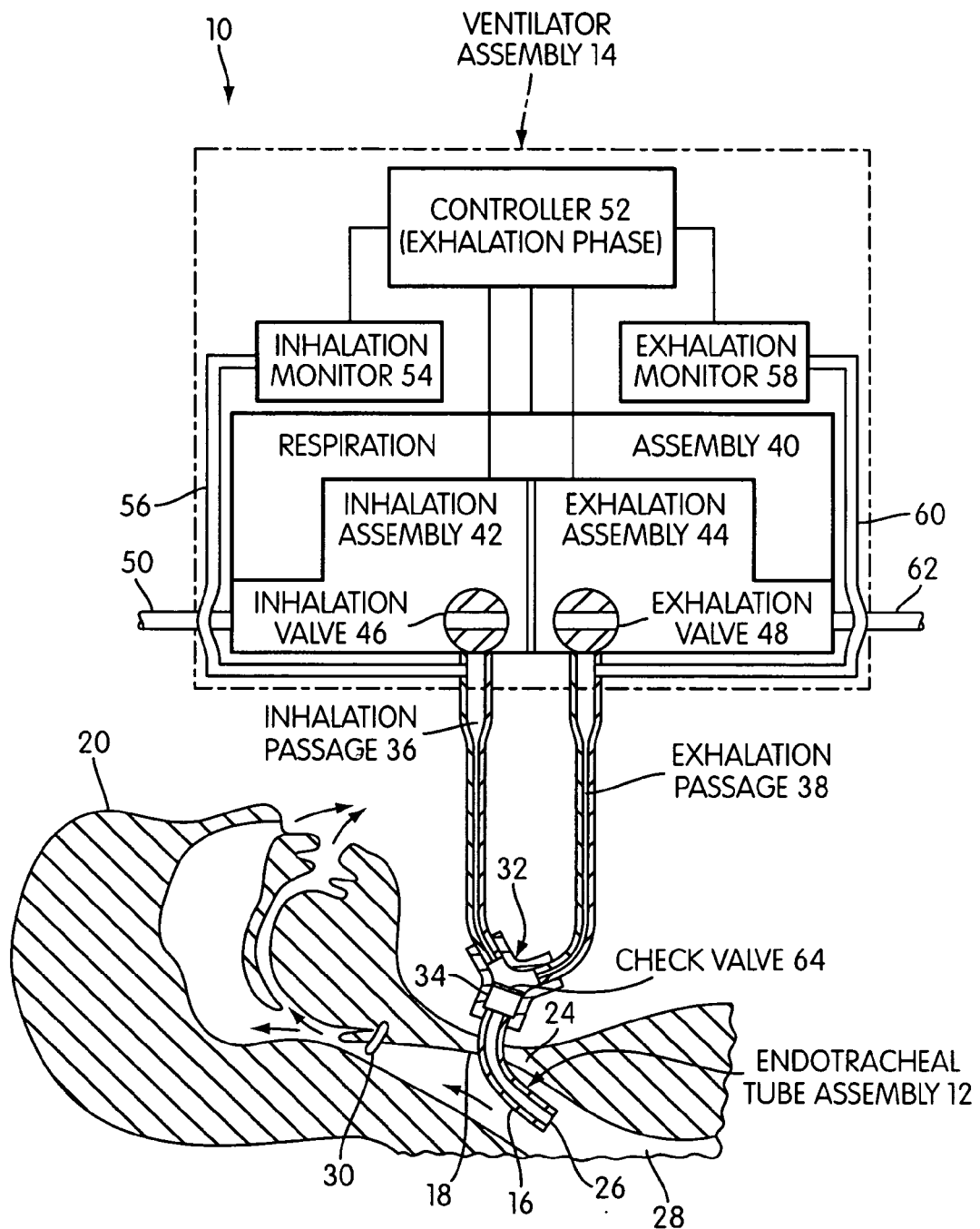
FIG. 5A is a view similar to FIG. 4A, but showing arrows indicating the direction of flow when the valves and controller are in an exhalation phase.
Figure 5B:
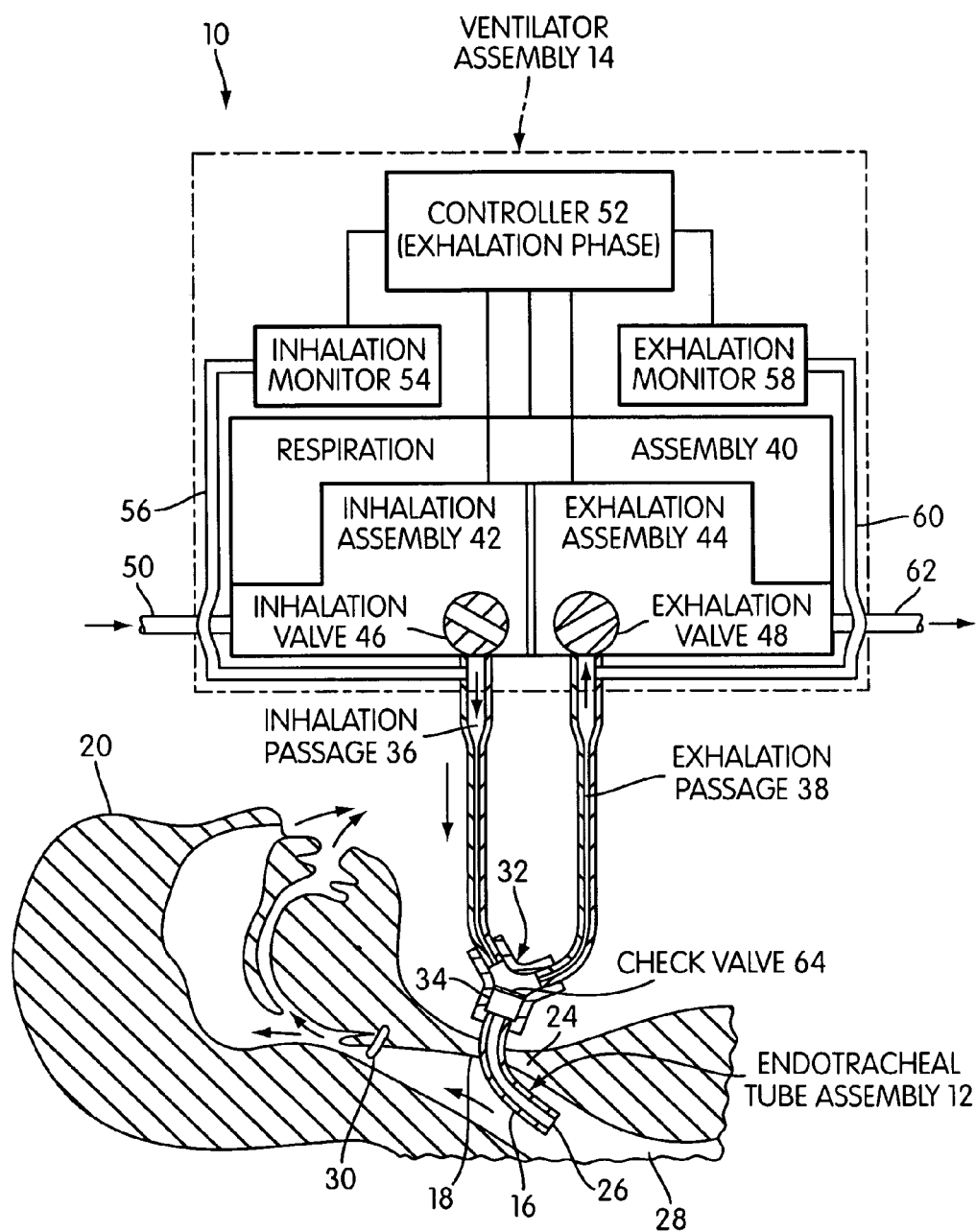
FIG. 5B is a view similar to FIG. 5A, but showing partially closed exhalation and inhalation valves.

Note that FIG. 4B is functionally the same as 4A, but showing a partially closed exhalation valve, while FIG. 5B is functionally the same as FIG. 5A, but showing partially closed inhalation and exhalation valves.

As noted above, controller 52 will regulate exhalation valve 48 so as to be relatively closed during the exhalation phase, when the inhalation valve 46 is relatively closed, and the pressure in exhalation passage 38 will be generally equal to the patient's airway pressure throughout the exhalation phase. Since this pressure reduces in the patient's airway as the exhalation phase proceeds, the exhalation monitor can continue during the exhalation phase to monitor the patients reducing airway pressure. Because the closed (or partially closed) inhalation valve 46 and closed (or partially closed) exhalation valve 48 will maintain the pressure within the communicating inhalation passage 36 and exhalation passage 38 at or slightly above the pressure in the patient's lungs during the exhalation phase, and because this pressure is approximately balanced with the pressure in the patient's lungs through operation of the check valve 64, exhalation monitor 58 (and/or inhalation monitor 54) is/are able to effectively approximate the pressure in the patient's lungs at all times during the exhalation phase. Consequently, as the patient's airway pressure diminishes during the exhalation phase, the pressure closed within communicating passages 36 and 38 will continue to equalize with the patient's airway pressure during the exhalation phase. Exhalation monitor 58 is thus monitoring the patient's airway pressure during the exhalation phase rather than atmospheric pressure, as would be the case if the exhalation valve were to open.

Figure 6:
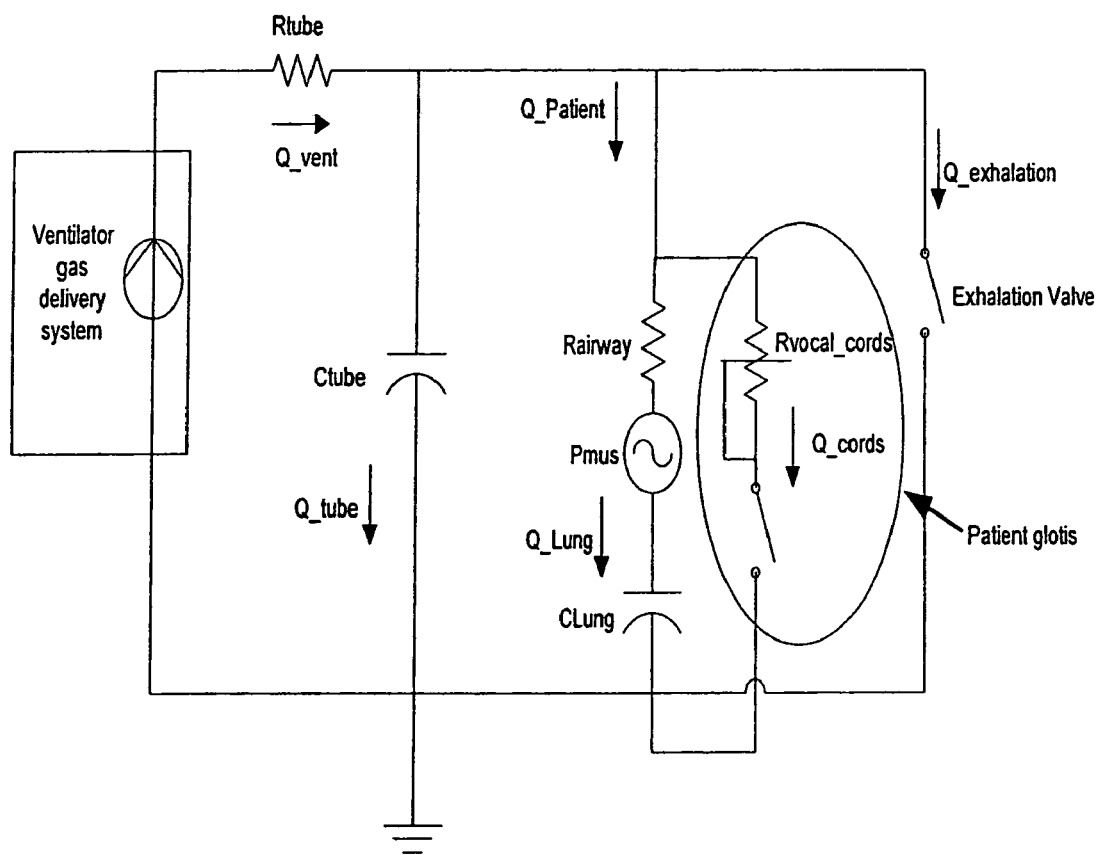
FIG. 6 schematically depicts the system of FIGS. 1 and 2 as an analogous electric circuit diagram, and showing an arrangement in which the exhalation valve is completely closed during the inhalation and exhalation phases.

FIG. 6 schematically depicts the system of FIGS. 1 and 2 as an analogous electrical circuit diagram.

In FIG. 6, the various components of the system shown in FIGS. 1 and 2 are depicted as electrical symbols as known in the art, each labeled with a descriptive word or descriptive abbreviation. The descriptive abbreviations are as follows: Rvocal_cords refers to the patient's vocal cord resistance. Rvocal_cords is shown as a variable resistor to show the variable resistance generated by the vocal cords (for example, higher pitch sounds generate greater resistance). Rairway refers to the patient's airway resistance. Rtube refers to the patient's circuit tubing resistance or conduit resistance. Ctube refers to the patient's circuit tubing compliance or conduit compliance, which can be measured as a capacitance, or the volume of tubing divided by the pressure in the tubing. Clung refers to the patient's lung compliance. Pmus refers to the pressure created in the patient's lungs by the patient's muscles, and illustrated as an alternating pressure generated by the patient through the patient's muscle action (e.g., patient's diaphragm, intercostal muscles, pectoral muscles, etc.).

The prefix letter Q refers to a quantity of gas flow delivered by the ventilator (Q_vent) or by the patient during the exhalation phase (Q_exhalation). The Q prefix also refers to a quantity of gas flow delivered (1) to the conduit or tubing system (Q_tube), (2) to the patient (Q_patient), (3) to the patient's lungs (Q_lung) and (4) to the patient's vocal cords (Q_cords).

As shown in FIG. 6, gas flow is delivered by the ventilator (Q_vent) during the inhalation phase of the breathing cycle. Because the exhalation valve is closed (i.e., switch open) during this phase, gas is delivered to the patient (Q_patient) as well as the tubing system (Q_tube). During the inhalation phase, the flow through the vocal cords (Q_cords) is typically zero, as the patient's glottis is closed (represented by the open switch next to Q_cords in FIG. 6) so the gas (Q_Lung) is delivered to the patient's lungs. However, it should be appreciated that in some instances during the inhalation phase, the gas being delivered by the ventilator can be used for speech purposes by the patients, and so the flow through vocal cords is not zero.

It should be appreciated that the open switch in FIG. 6 labeled "Exhalation Valve" represents an arrangement wherein the exhalation valve is completely closed for both inhalation and exhalation phases. This switch can be replaced by a variable resistor to reflect arrangements wherein the exhalation valve may be partially or relatively closed during exhalation and/or inhalation phases.

Generally, the exhalation phase of the breathing cycle is when talking is facilitated. Talking is accomplished by increasing the pressure in the lung via the thoracic muscle recoil forces as well as diaphragmatic muscle activity. During speech, the direction of Q_Lung is reversed and leaves the patient through the vocal cords. Modulation of the vocal cords (i.e., vocal cords' resistance variation) is responsible for the cords vibrations which ultimately become speech.

During the exhalation phase, the ventilator's exhalation valve remains closed (or partially closed), and in this way, the majority of the gas flow is redirected towards the vocal cords during speech. During exhalation, a small amount of gas may flow towards the tubing system compliance. This compliance, typically less than 2 ml/cmH$_2$O, being small compared to the patient Lung compliance (Clung) uses a few milliliters of the gas volume exhaled by the patient.

The embodiments just described without the speaking valve (check valve) have several advantages, including, but not limited to, the following:

1) Allows detection of inflated tracheotomy tube cuffs. This is possible since the ventilator pressure sensors are able to monitor the pressure in the tubing system and this pressure in turn reflects the pressure in the patient's airway and lungs.

2) Allows assessment of the patient's airway pressure during exhalation so that stacking of breaths is avoided. This is not practical in embodiments using the speaking valve, since the valve blocks the pneumatic communication with the ventilator's pressure transducers.

3) Allows for strong patient coughs without interference from a one way valve's membrane, since no valve is used.

4) Allows aerosol treatments without the need to take out the speaking valve.

5) Allows suctioning without the need to take out the speaking valve.

6) Avoids the need to take out the speaking valve to prevent the valve's disc/membrane from becoming clogged with sputum, since no speaking valve is required.

Note that embodiments where the speaking valve is present, the volume of gas trapped in the tubing circuit can only escape through the speaking valve. Gas flow through the speaking valve is possible only if there exists a pressure differential across the valve. Thus, monitoring of the pressure in the patient's airway and lungs via monitoring of the tubing system pressure is possible, so long as the pressure in conduit assembly 32 is greater than or equal to the pressure in the patient's lungs, which is the manner of operation of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of operating a ventilator assembly that includes a conduit providing inhalation and exhalation passages communicating with one another, and a respiration assembly capable of performing respiratory cycles including (1) an inhalation phase during which (a) a proportionally controlled inhalation valve communicating with the inhalation passage is relatively open for the passage of gas therethrough into the inhalation passage and to a patient, and (b) a proportionally controlled exhalation valve between the exhalation passage and an exhalation outlet in the ventilator assembly is relatively closed, and (2) an exhalation phase having a talking mode during which the proportionally controlled inhalation valve is relatively closed, restricting inhalation gas from the patient and the atmosphere, and the exhalation valve is relatively closed, and a non-talking mode during which the proportionally controlled inhalation valve is relatively closed, restricting inhalation gas from the patient and the atmosphere, and the proportionally controlled exhalation valve is relatively open, the method comprising acts of:

operating the respiration assembly through respiratory cycles by a respiration assembly controller controlling the proportionally controlled inhalation and exhalation valves so that during the inhalation phase, the gas in the inhalation passage flows through a tube into the patient's airway and lungs with the tube inserted below the patient's vocal cords, and during the exhalation phase, the proportionally controlled exhalation valve is maintained relatively closed and the patient is allowed to exhale the gases in the patient's airway and lungs, around the tube and past the patient's vocal cords and out of the patient's mouth, thereby facilitating the patient's ability to speak, and monitoring the pressure within at least one of the passages during the inhalation and exhalation phases for purposes of determining a pressure within the patient for use in operating the ventilator assembly by controlling at least one of the proportionally controlled inhalation and exhalation valves, to regulate a desired pressure in at least one of the passages and the patient during both phases, further assisting the patient to talk during the exhalation phase.

2. The method as defined in claim 1, wherein the tube is devoid of a check valve so that gas exhaled by the patient during each exhalation phase is communicated with the passages while both inhalation and exhalation valves are closed.

3. The method as defined in claim 1, wherein the tube has a check valve so that the gas exhaled by the patient during each exhalation phase is prevented from communicating with the passages.

4. The method as defined in claim 1, wherein during the inhalation phase, the inhalation valve is completely open.

5. The method as defined in claim 1, wherein during the inhalation phase the exhalation valve is completely closable and prevents any gas passage therethrough.

6. The method as defined in claim 1, wherein during the exhalation phase the inhalation valve is completely closable and prevents any gas passage therethrough.

7. The method as defined in claim 1, wherein during the exhalation phase, the inhalation valve is controlled to regulate pressure in the conduit to facilitate the patient's ability to speak.

8. The method as defined in claim 1, wherein during the exhalation phase, the exhalation valve is completely closable and prevents any gas passage therethrough.

9. The method as defined in claim 1, wherein during the exhalation phase, the exhalation valve is controlled to regulate pressure in the conduit to facilitate the patient's ability to speak.

10. The method as defined in claim 1, wherein the monitoring is used to perform one or more of control the inhalation valve and the exhalation valve, detect patient airway blockages, detect that at least a portion of the conduit has been disconnected, and detect occlusions in the conduit.

* * * * *